US009322705B2

(12) United States Patent
Hovinen et al.

(10) Patent No.: US 9,322,705 B2
(45) Date of Patent: Apr. 26, 2016

(54) SENSING A SELECTED AMBIENT ENVIRONMENT

(75) Inventors: Minna Helena Hovinen, Edina, MN (US); Oliver Ye Tao, Eden Prairie, MN (US)

(73) Assignee: SEAGATE TECHNOLOGY LLC, Cupertino, CA (US)

( * ) Notice: Subject to any disclaimer, the term of this patent is extended or adjusted under 35 U.S.C. 154(b) by 553 days.

(21) Appl. No.: 13/596,957

(22) Filed: Aug. 28, 2012

(65) Prior Publication Data

US 2014/0061446 A1    Mar. 6, 2014

(51) Int. Cl.
| G01N 21/85 | (2006.01) |
| G01J 1/42 | (2006.01) |
| G01N 21/41 | (2006.01) |
| G11B 25/04 | (2006.01) |
| G11B 33/14 | (2006.01) |

(52) U.S. Cl.
CPC . *G01J 1/42* (2013.01); *G01N 21/41* (2013.01); *G11B 25/043* (2013.01); *G11B 33/148* (2013.01)

(58) Field of Classification Search
CPC .............. G01N 21/85; G01N 21/8507; G01N 2021/8578
USPC ........ 250/573–576, 214 AL, 214 B; 356/436, 356/437, 439, 445; 73/19.01, 23.2, 31.01, 73/335.01

See application file for complete search history.

(56) References Cited

U.S. PATENT DOCUMENTS

| 4,661,320 | A |   | 4/1987 | Ito et al. |
| 4,907,441 | A | * | 3/1990 | Shurmer ..................... 73/23.2 |
| 5,201,220 | A | * | 4/1993 | Mullins et al. ............ 73/152.42 |
| 5,734,165 | A |   | 3/1998 | Unal et al. |
| 6,016,203 | A |   | 1/2000 | Martin |
| 6,577,396 | B1| * | 6/2003 | Naya ........................... 356/445 |
| 6,921,899 | B2|   | 7/2005 | Martin |
| 7,382,459 | B2|   | 6/2008 | Ludwig |
| 7,449,694 | B2|   | 11/2008 | Yi et al. |
| 7,489,835 | B1|   | 2/2009 | Xia et al. |
| 7,564,032 | B2|   | 7/2009 | Boekelman |
| 7,564,558 | B2|   | 7/2009 | Martin |
| 7,817,259 | B2|   | 10/2010 | Smith et al. |
| 7,864,326 | B2|   | 1/2011 | Cox et al. |
| 2006/0086903 | A1|   | 4/2006 | Hopkins et al. |

\* cited by examiner

*Primary Examiner* — Kevin Pyo
(74) *Attorney, Agent, or Firm* — Hall Estill Attorneys At Law

(57) ABSTRACT

An apparatus and associated method using a light source selectively emitting an incident beam. A thin film is disposed in a path of and responsive to the incident beam to produce a reflected beam. A light-sensing probe is capable of detecting the reflected beam. Ambient environment logic responsive to the light-sensing probe compares a position of the reflected beam to an expected position to make a characteristic determination of a selected ambient environment through which the incident beam propagated.

20 Claims, 6 Drawing Sheets

SENSING A SELECTED AMBIENT ENVIRONMENT

SUMMARY

Embodiments of the present invention contemplate a light source selectively emitting an incident beam. A thin film is disposed in a path of and responsive to the incident beam to produce a reflected beam. A light-sensing probe is capable of detecting the reflected beam. Ambient environment logic is responsive to the light-sensing probe to compare a position of the reflected beam to an expected position to make a qualitative determination of a selected ambient environment through which the incident beam propagated.

Embodiments of the present invention contemplate an ambient environment characterization device having computer instructions stored in memory that are executable to perform computational logic. In response to an incident beam of light propagating through a selected ambient environment, the ambient environment characterization device compares a refractive index response associated with the incident beam of light to a predetermined threshold response to characterize the selected ambient environment in terms of a constituent makeup.

Embodiments of the present invention are directed to a method of characterizing a selected ambient environment. The method includes directing an incident beam of light through a selected ambient environment, reflecting the incident beam via a thin film device to produce a reflected beam, detecting a position of the reflected beam, comparing the position of the reflected beam to an expected position, and qualitatively characterizing the selected ambient environment in terms of results of the comparing step.

DETAILED DESCRIPTION

Figure 1:
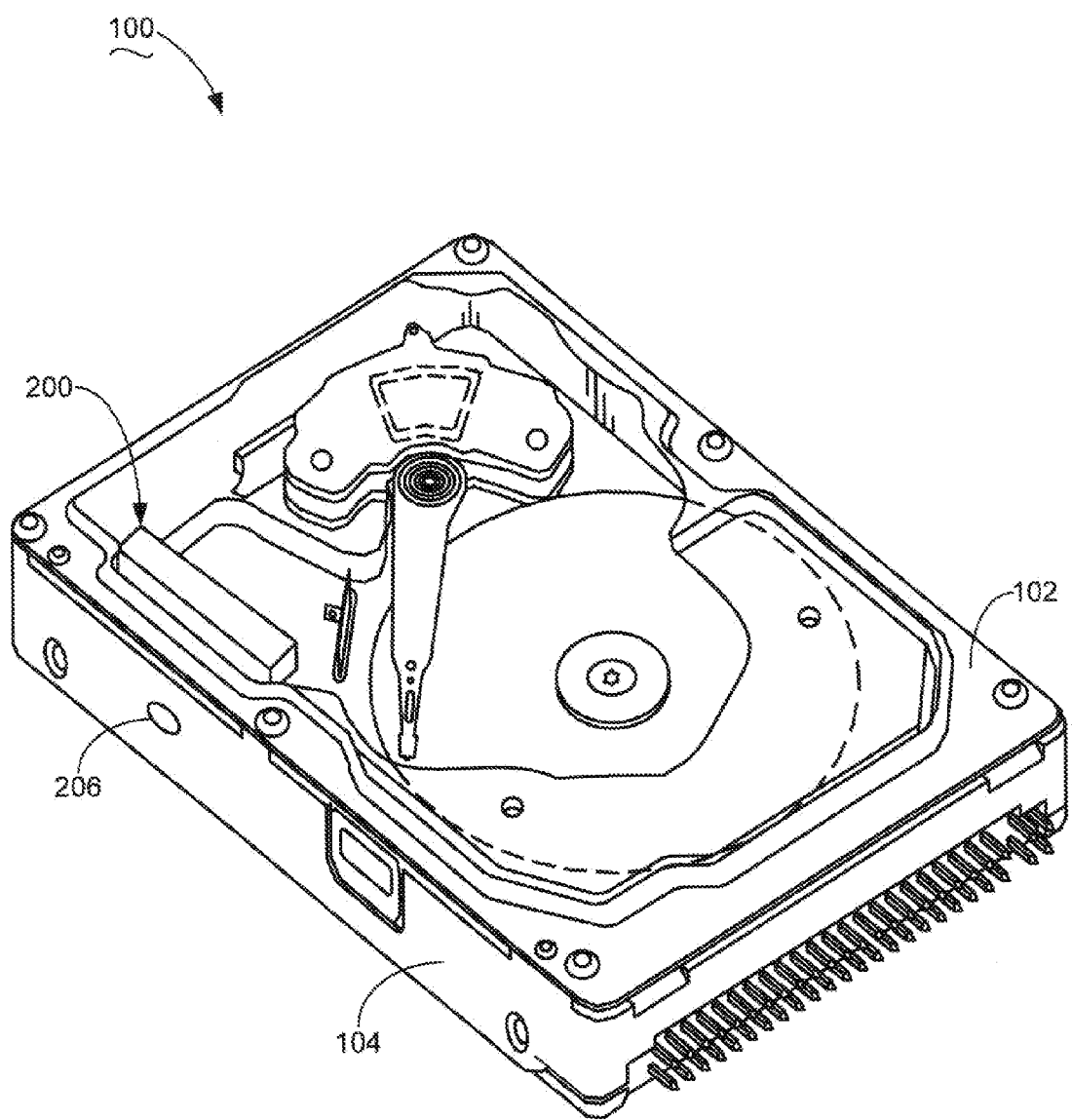
FIG. 1 is an isometric view of a data storage device suited for carrying out illustrative embodiments of the present invention.

Gas sensors are used to detect the presence of a particular gas, or a particular concentration of a gas, in an enclosed environment. Many of the gas sensors constructed in accordance with previously attempted solutions are large complex systems that are expensive to construct and maintain. There are numerous types of gas sensors that use various technologies, most relying on gas absorption or reaction in order to detect gas. For example, one type of gas sensor detects the presence of gas based on a chemical reaction between the gas and the sensor. Another type uses optical technology and gas is sensed based on spectroscopic measurement of the absorption spectra. Other types of sensors rely on a reaction between the gas and a media in order to detect a gas. Other types of gas sensors include smoke detectors which use light intensity detection which detect when particles scatter light.

Optical technology requires special optics and environmental enclosures due to the absorption resonance frequencies at the infrared light region required by these systems. In other systems, optical fibers are used where light propagation in the fiber is altered by the measurable interest, which in the case of gas sensors involve gas absorption or reaction with the fiber material.

The stability and accuracy of the gas sensor are influenced by the mechanical strength, thermal drift, humidity levels, age of the light source and detector, etc. Due to these factors, deviations within the known systems are common. These inherent limitations of the previously attempted solutions become ever more problematic in detecting inert and elemental gases with any degree of reliability.

A gas sensor in accordance with the claimed embodiments is described below that is used to detect and/or monitor reactive, elemental and inert gases in an ambient environment. The gas sensor uses a thin film to refract and reflect an incident light beam. The positional change of the incident beam is detected via a light-sensing probe, and logic responsive to the light-sensing probe is used to make a characteristic determination, perhaps qualitative or quantitative, of the gas present in a space being monitored.

Generally, the disclosed embodiments contemplate monitoring for the presence of a selected ambient environment in a monitored space, such as an enclosed space. The skilled artisan will readily understand the present embodiments are useable in performing gas sensing and monitoring in a multitude of processing and operations environments. Controlled manufacturing and mining environments, for example, are ideally suited for applying the embodiments generally contemplated herein and disclosed by illustrative teaching embodiments. Maintaining an environmental presence of a desired constituent inside a containerized space, such as where a brazing or a welding operation is being conducted, is just one useful application of the embodiments of the present invention. As such, an enumeration of all useful applications of the present embodiments is not necessary for the skilled artisan to comprehend the claimed scope of the present embodiments.

Referring to the drawings in general, and more particularly to FIG. 1 that shows an isometric view of a data storage device 100 (or "drive") suited for carrying out illustrative embodiments of the present invention. Again, although the following description describes an illustrative apparatus and method used in precisely sensing and monitoring gases contained within the drive 100, the present embodiments as contemplated herein and as claimed are not so limited. The drive 100 can be alternatively embodied by a container suited for containing an environment.

The drive 100 has an enclosure formed by attaching a cover (shown cutaway) 102 to a base 104 with a seal therebetween. Components of the drive 100 are contained in the enclosure to protect them from debris in the external environment. It can also be advantageous to seal the enclosure sufficiently to contain a desired working fluid in the enclosure, such as helium, to enhance performance of the drive. The amount of helium can be set at a threshold concentration level, which is illustrative of the term "selected ambient environment" used herein. The present embodiments contemplate a gas sensor 200 and an associated method for monitoring the enclosure to ensure that the selected ambient environment is maintained.

Figure 2:
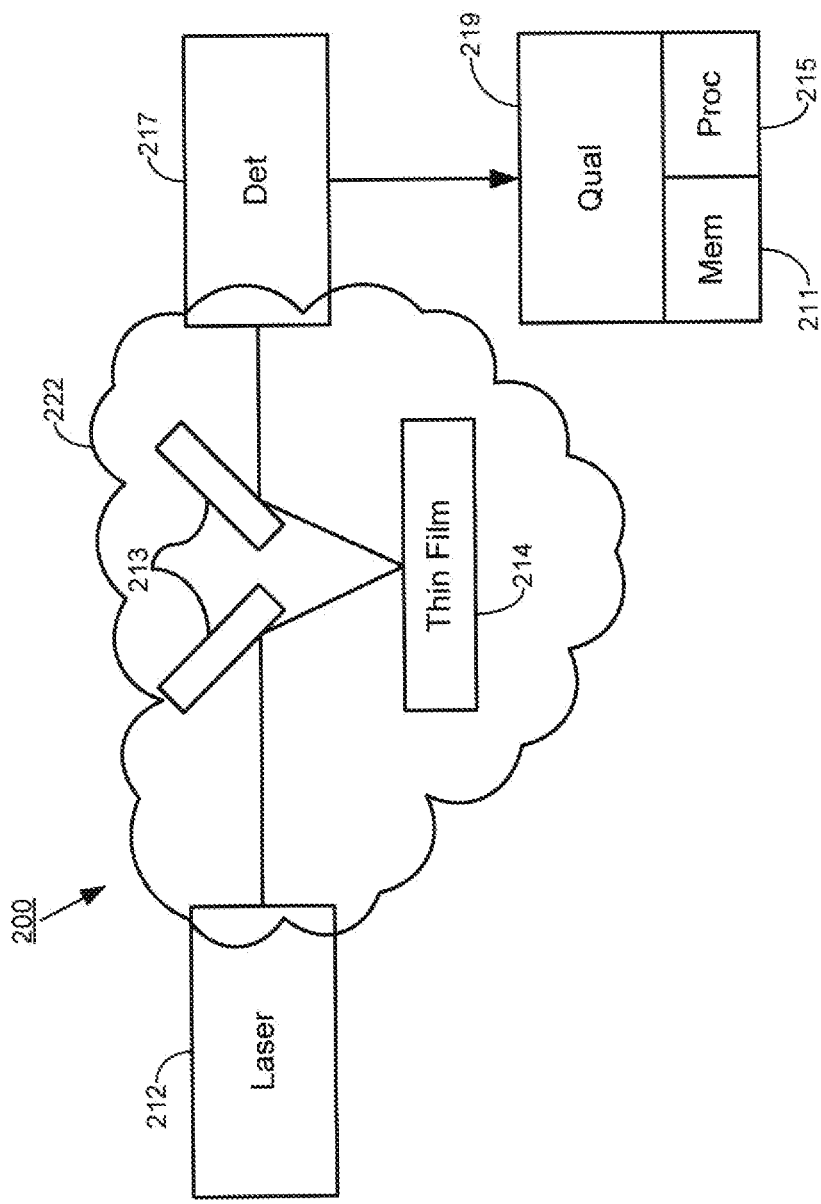
FIG. 2 is a diagrammatic depiction of the gas sensor of FIG. 1 in accordance with embodiments of the present invention.

FIG. 2 is a diagrammatic depiction of the gas sensor 200 in accordance with embodiments of the present invention. Generally, the gas sensor 200 is sensitive to changes in light refraction due to changes in the ambient environment through which a light beam propagates. A light source 212 emits a light beam that is reflected by a thin film 214 to a light-sensing probe 217. In some embodiments the light source 212 can be included as a component in the gas sensor 200 depicted in the enclosure in FIG. 1. Alternatively, to reduce cost or save space a sealed transparent window 206 (FIG. 1) can be provided in the enclosure for transmitting the incident beam from an external light source. The light-sensing probe 217 is coupled to a characterization module 219 that is a processor 215 based device selectively executing computational logic stored in a memory 211. The computational logic can be but is not limited to circuit logic, computer instructions stored in memory, i.e. software logic, or a combination thereof. The computational logic operably compares an expected position of the light beam, corresponding to a known selected ambient environment, to the observed position of the light beam to characterize the environment 228 through which the incident beam propagates. In some embodiments mirrors 213 can be used to direct the light beams.

Figure 3:
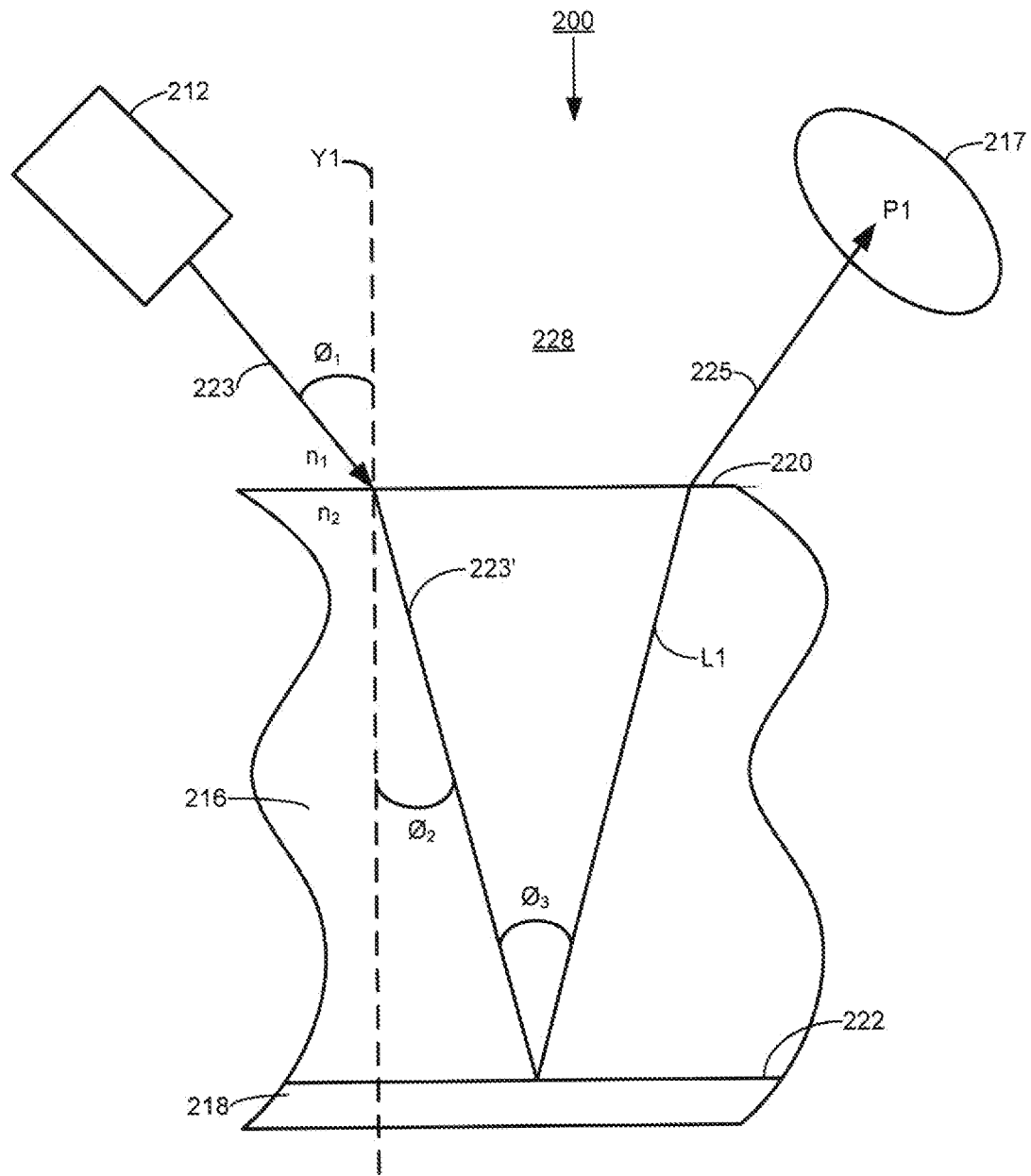
FIG. 3 is a diagrammatic depiction of the refraction and deflection of the incident beam in a thin film in accordance with embodiments of this invention.

FIG. 3 illustrates details of the refraction and deflection of the incident beam in the thin film depicted in FIG. 2. The light source 212 provides a directional beam of a single wavelength, e.g. a laser. The thin film 214 has an optically transparent material 216 and a reflective layer 218 having a reflective surface 222. In some embodiments, the optically transparent material 216 can be dielectric. The optically transparent material 216 has an exposed surface 220. The reflective layer 218 can be any material that is reflective, e.g. a metal, a semiconductor material, etc. The light-sensing probe 217 measures a position of the reflected beam 225, and can measure small deviations in that position. The light-sensing probe 217 can be, but is not limited to, for example, a beam position detector or a charge coupled device (CCD). The CCD can be a semiconductor device with an array of light sensing elements in a known geometric arrangement. The position of the reflected beam 225 is sensed by the CCD.

As shown in the embodiments of FIG. 3, the incident beam 223 propagates through an ambient environment 228, having a first refractive index $n_1$. The optically transparent material 216 has a different refraction index $n_2$. The refractive index n of any medium is defined as the ratio of the speed of light in a vacuum to the speed of light in the medium. By definition, a vacuum has a refractive index n of 1.0 and gases have refractive indexes in the range of 1.0001 to 1.01. The incident beam 223 refracts relative to an angle of incidence $\theta_1$ from normal based on an axis Y1 that is perpendicular to the surface 220. The incident beam 223 passes through the surface 220 of the optically transparent material 216, and based on the refractive indexes $n_1$, $n_2$ the incident beam 223 characteristically refracts at the surface 220.

Due to the refraction, the direction of the incident beam 223 is altered resulting in refracted beam 223'. The refracted beam 223' has an angle of refraction $\theta_2$ from normal Y1. The refracted beam travels a distance L1 through the optically transparent material 216 and reaches the reflective surface 222 of the reflective layer 218. The light beam 223' is reflected symmetrically, at reflected angle $\theta_3$, and travels the distance L1 through the optically transparent material 216 to the surface 220. The reflected beam 223' again refracts at the surface 220 to form a reflected beam 225 through the ambient environment 228 directed to the light-sensing probe 217. The light-sensing probe 217 detects the position P1 of the reflected beam 225. Logic that is responsive to the light-sensing probe 217 can store this positional information in memory 211 (FIG. 2).

The refracted beam 223' as described above can be predicted by application of Snell's law in terms of the relationship between the angles of incidence $\theta_1$ and refraction $\theta_2$ for light passing through a boundary between two different isotropic media (e.g. air 228 and the optically transparent material 216). The ratio of the sines of the angles of incidence $\theta_1$ and refraction $\theta_2$ is equivalent to the ratio of phase velocities in the two media and equivalent to the opposite ratio of the indices of refraction:

$$\frac{\sin\theta_1}{\sin\theta_2} = \frac{v_1}{v_2} = \frac{n_2}{n_1}$$

with each $\theta$ as the angle measured from the normal, v as the velocity of light in the respective medium (SI units are meters per second, or m/s) and n as the refractive index (which is unitless) of the respective medium.

Figure 4:
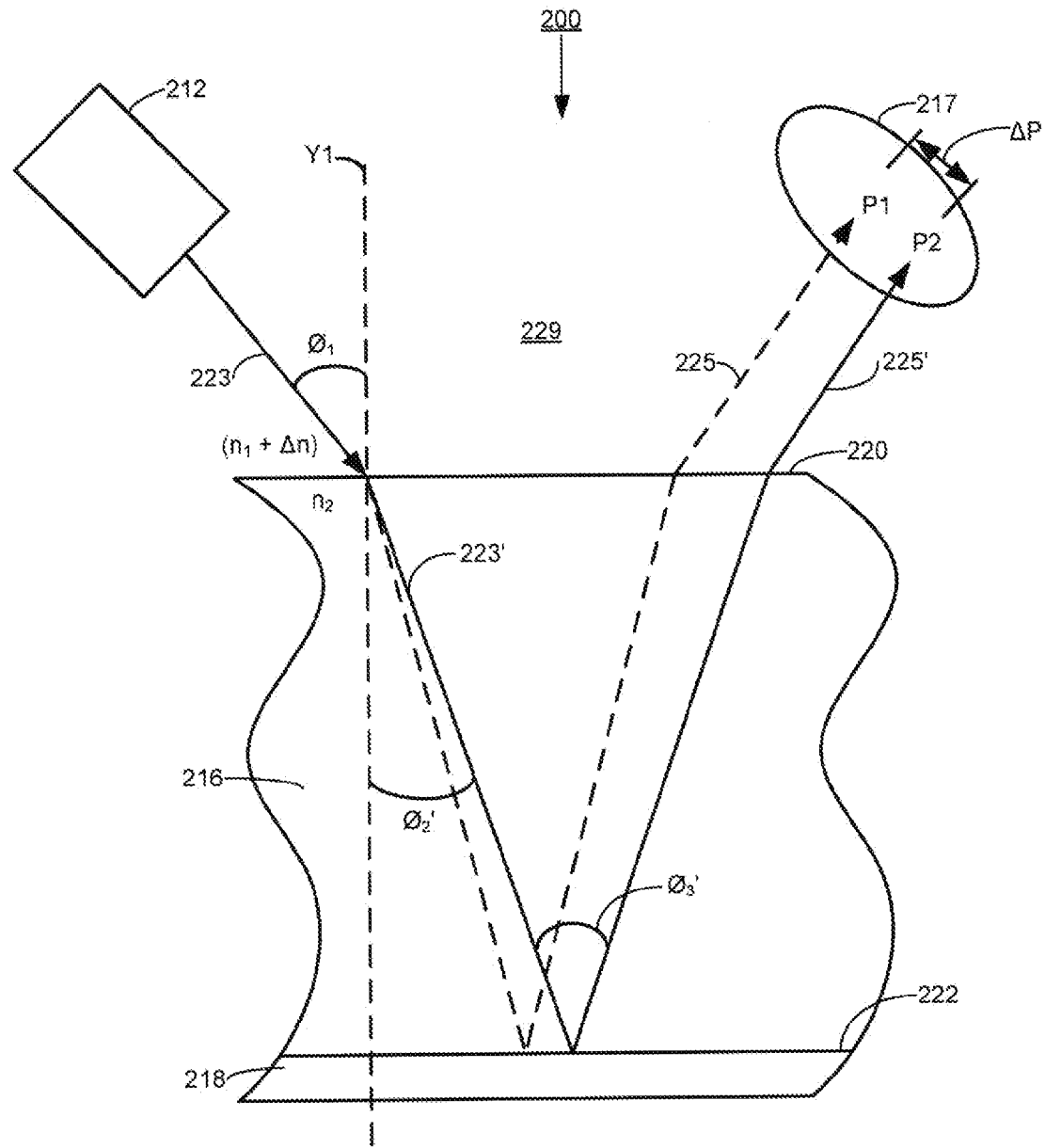
FIG. 4 is a diagrammatic depiction of the changes in refraction and deflection of the incident beam in response to changes in the selected ambient environment.

As is illustrated in the embodiments of FIG. 4, a different ambient environment 229 changes the refractive index from $n_1$ to $(m+\Delta n)$. The change in ambient environment can be due to a different gas being present, or can be due to a change in concentration of the given gas. Changing the refractive index from $n_1$ to $(m+\Delta n)$ correspondingly changes the angle of refraction $\theta_2$ such that, in some embodiments, the new angle of refraction $\theta_2'$ is larger than $\theta_2$. In other embodiments, the new angle of refraction $\theta_2'$ can be smaller than $\theta_2$. This angle of refraction $\theta_2'$ changes the location and angle $\theta_3'$ where the refracted beam reflects from the reflective surface 222, where $(\theta_{3+}\Delta\theta=\theta_3')$. This widening or narrowing of the angle translates into the reflected light beam 225' striking the light-sensing probe 217 at a position P2, different than the position P1 described previously. The computational logic that is responsive to the light-sensing probe compares P1 and P2 and determines the difference in beam position $\Delta P$. Based on $\Delta P$, the sensor 200 can qualitatively determine whether the selected ambient environment exists in the monitored space. In some embodiments, the computational logic can quantitatively characterize the ambient environment. For example, where the gas type is known, and predefined baseline datum has been stored, it is possible to determine the concentration of the gas in the ambient environment. Conversely, if the concentration is known, it is possible to determine the type of gas in the ambient environment.

It is contemplated that the gas sensor 200 can be used as a gas monitoring system. The gas sensor 200 can operate to monitor a predetermined threshold concentration of gas (the selected ambient environment) and to signal a warning, or even disable the system, if the selected ambient environment is compromised. In some embodiments, the gas sensor 200 continually monitors the environment, while in other embodiments the gas sensor 200 periodically samples the environment.

Figure 5:
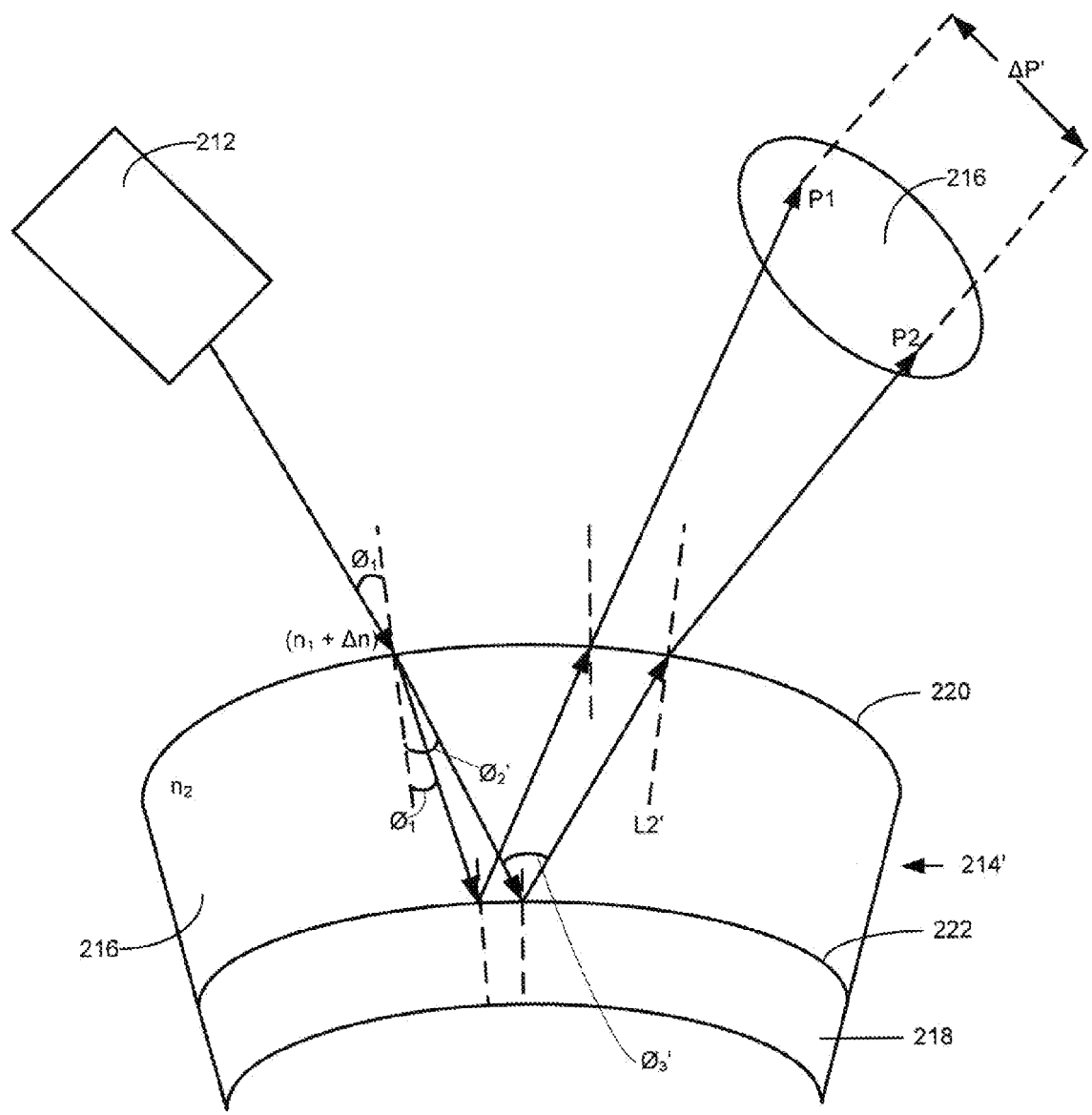
FIG. 5 is a diagrammatic depiction similar to FIG. 4 but where the thin film has a convex curvature.

Depending on the refractive index of the gas, the change in angle $\theta_3'$ from $\theta_3$ may be extremely small, meaning the gas sensor 200 must be capable of discerning small $\Delta P$s. For example, nitrogen has a refractive index of 1.00029839 at 0.5876 µm. Therefore, nitrogen is extremely difficult to detect. As illustrated in FIG. 5, increased sensitivity can be obtained by employing a curvilinear to the thin film 214'. Nitrogen detection was successfully achieved in reducing these embodiments to practice using visible laser light refraction in aluminum oxide films on curved metal.

Sensitivity can be determined taking the first derivative of Snell's law, the derivative of the angle of refraction to the refractive index of the ambient environment (for a fixed incident angle and given film index $n_2$):

$$\frac{d\theta_2}{dn_1} = \tan\theta_2 \frac{1}{n_2}$$

To obtain a higher sensitivity, a film can be selected a having a higher refraction angle $\theta_2$ and a lower refractive index $n_2$. However, the refraction angle $\theta_2$ not only depends on the film material itself but also on the incident angle $\theta_1$ where the higher the incident angle $\theta_1$, the higher the refraction angle $\theta_2$. Therefore, a higher incident angle $\theta_1$ will give a higher sensitivity until the angle of total reflection is reached.

In the embodiments shown in FIG. 5, the curvature of the thin film 214' is convex in relation to the path of the incident beam. The convex curvature correspondingly increases the reflected angle $\theta_3$ such that the difference in beam position $\Delta P'$ is necessarily increased over that of $\Delta P$ discussed above for the linear thin film 214. The sensitivity of the gas sensor system 200 is inversely related to the radius of the curvature.

Figure 6:
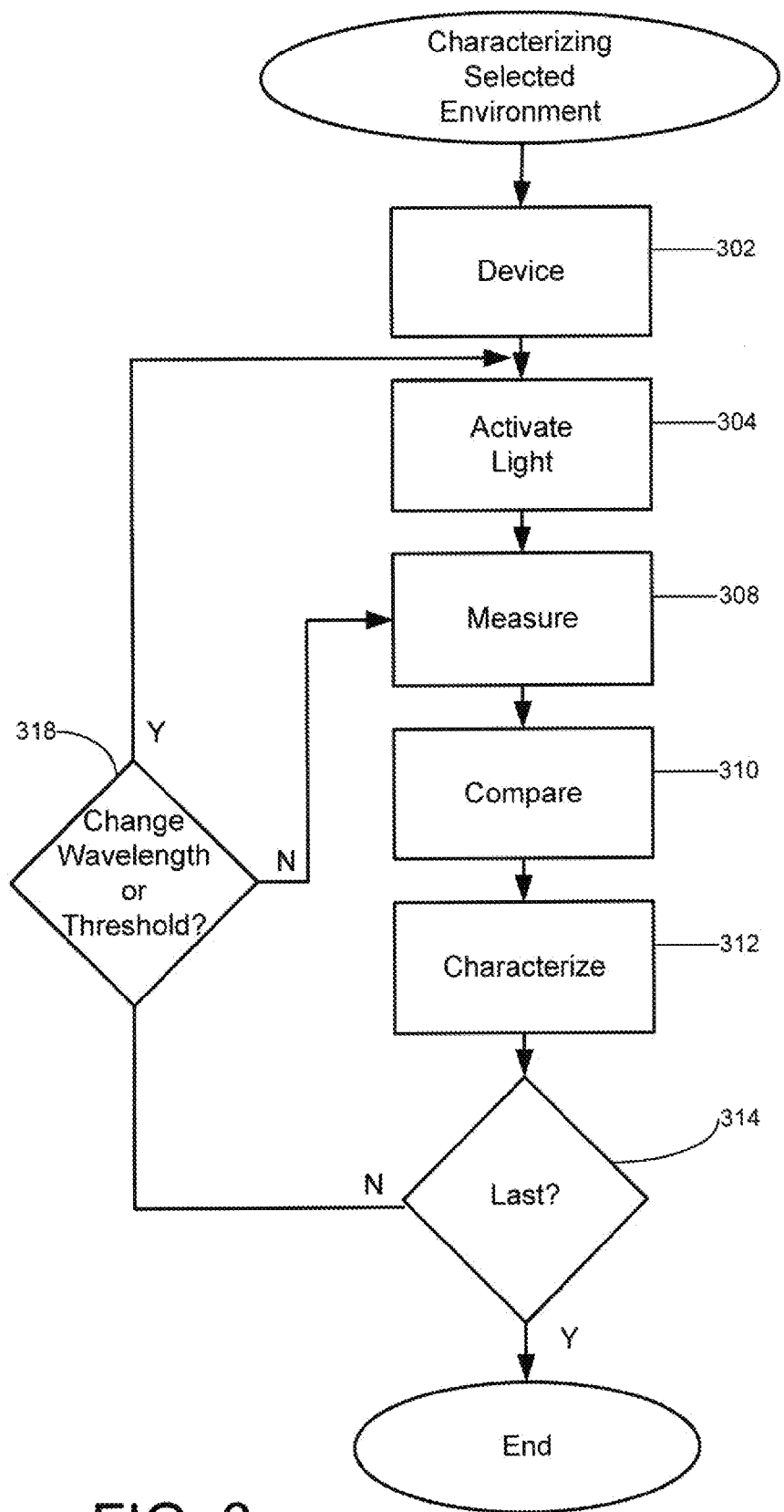
FIG. 6 is a flowchart of steps in a method for CHARACTERIZING A SELECTED ENVIRONMENT in accordance with embodiments of the present invention.

FIG. 6 is a flowchart depicting steps executed by the computational logic in the memory 211 (FIG. 2) and executed by the processor 215 (FIG. 2) in the characterization module 219 to characterize the selected ambient environment. The method begins in block 302 with obtaining the characterization device as described that characterizes the incident beam. The method continues in block 304 by activating the light source and directing the incident beam through the selected ambient environment. The incident beam is refracted and reflected via the thin film to the light-sensing probe. At block 308, the light-sensing probe measures the position of the reflected beam.

Control then passes to block 310 where the position of the reflected beam measured in block 308 is compared to a threshold position, or in other words, to an expected value for the selected ambient environment. In block 312 a characterization of the selected ambient environment is determined. For example, if the measured position in block 308 is greater than a threshold as determined in block 310 then the sensor 200 indicates that the selected ambient environment exists in the monitored space.

In block 314 it is determined whether the last light beam has been tested. If the determination of block 314 is yes, then the method ends. Otherwise, control passes to block 318 where it is determined whether it would be advantageous to adjust the wavelength of the incident beam and/or the threshold value of the expected position. If the determination of block 318 is yes, then control passes to block 304 for reactivation of the light source and associated computational logic. Doing so would permit testing at two or more different wavelengths and against the associated thresholds. Doing so would also permit adjusting the threshold for a particular wavelength, as might be advantageous under statistical process control when it indicates that the process is performing at less than an expected capability due to observed process variation. If the determination of block 318 is no, then control passes to block 308 and the reflected beam is again measured and the position is determined.

It is to be understood that even though numerous characteristics and advantages of various aspects have been set forth in the foregoing description, together with details of the structure and function, this disclosure is illustrative only, and changes may be made in detail, especially in matters of structure and arrangement to the full extent indicated by the broad general meaning of the terms in which the appended claims are expressed.

The invention claimed is:

1. An apparatus comprising:
a light source selectively emitting an incident beam into an ambient environment;
a thin film disposed in a path of the incident beam in the ambient environment to produce a reflected beam;
a light-sensing probe capable of detecting the reflected beam; and
ambient environment logic including computer instructions stored in computer memory and configured to be executed by computer processor to respond to the light-sensing probe to compare a position of the reflected beam to an expected position to make a characteristic determination of a selected ambient environment through which the incident beam propagated.

2. The apparatus of claim 1, the thin film comprising an optically transparent film disposed on a reflective surface.

3. The apparatus of claim 2, wherein the optically transparent film is a dielectric.

4. The apparatus of claim 1, wherein the thin film comprises an arcuate surface with a convex curvature in relation to the path of the incident beam.

5. The apparatus of claim 1 wherein the characteristic determination is a quantitative determination.

6. The apparatus of claim 5, wherein the ambient environment logic is responsive to changes in the observed position of the reflected beam.

7. The apparatus of claim 1 wherein the ambient environment logic is configured to compare a refractive index response associated with the incident beam of light to a predetermined threshold response to characterize the selected ambient environment in terms of a constituent makeup.

8. The apparatus of claim 7, wherein the refractive index response is defined by a first refractive index of the selected ambient environment and a second refractive index of a thin film where the thin film is an optically transparent film disposed on a reflective surface.

9. The apparatus of claim 8, wherein the optically transparent film is a dielectric.

10. The apparatus of claim 7, wherein the thin film comprises an arcuate surface with a convex curvature in relation to the propagation of the incident beam of light.

11. The apparatus of claim 7, wherein the constituent makeup of the selected ambient environment is a qualitative characterization.

12. The apparatus of claim 7, wherein the computational logic is responsive to changes in the observed comparison.

13. A method of characterizing a selected ambient environment, the method comprising:
directing an incident beam of light into the selected ambient environment;
reflecting the incident beam in the selected ambient environment via a thin film device to produce a reflected beam;
detecting a position of the reflected beam;
comparing the position of the reflected beam to an expected position; and
characterizing the selected ambient environment in terms of results of the comparing step.

14. The method of claim 13, wherein the reflecting step is characterized by the thin film being constructed of an optically transparent film disposed on a reflective surface.

15. The method of claim 14, wherein the reflecting step is characterized by the optically transparent film being constructed of a dielectric.

16. The method of claim 13, wherein the reflecting step is characterized by the thin film having an arcuate surface with a convex curvature in relation to the path of the incident beam.

17. The method of claim 13, wherein the comparing step is characterized by ambient environment logic responding to a light-sensing probe.

18. The method of claim 17, wherein the comparing step is characterized by the ambient environment logic signaling an alarm based on results of the comparing step.

19. The method of claim 16 wherein the convex curvature is selected in relation to a predetermined constituency of the selected ambient environment.

20. An apparatus comprising:
   a light source selectively emitting an incident beam;
   an optically transparent film with a reflective surface disposed in a path of the incident beam to produce a reflected beam;
   a light-sensing probe capable of detecting the reflected beam; and
   ambient environment logic including computer instructions stored in computer memory and configured to be executed by computer processor to respond to the light-sensing probe to compare a position of the reflected beam to an expected position to make a characteristic determination of a selected ambient environment through which the incident beam propagated.

* * * * *